United States Patent

Stenzel et al.

[11] Patent Number: 5,962,518
[45] Date of Patent: Oct. 5, 1999

[54] FUNGICIDAL ACTIVE COMPOUND COMBINATIONS

[75] Inventors: Klaus Stenzel, Düsseldorf; Wilhelm Brandes, Leichlingen; Stefan Dutzmann, Hilden; Bernd-Wieland Krüger, Bergisch Gladbach; Karl-Heinz Kuck, Langenfeld; Rolf Pontzen, Leichlingen; Thomas Seitz, Langenfeld, all of Germany; Atsumi Kamochi, Kochi; Ikuya Saitoh, Oyama, both of Japan

[73] Assignee: Bayer Aktiengesellschaft, Leverkusen, Germany

[21] Appl. No.: 08/943,349

[22] Filed: Oct. 1, 1997

Related U.S. Application Data

[63] Continuation of application No. 08/771,359, Dec. 16, 1996, abandoned, which is a continuation of application No. 08/541,777, Oct. 10, 1995, abandoned.

[30] Foreign Application Priority Data

Oct. 17, 1994 [DE] Germany .............................. 44 37 048

[51] Int. Cl.⁶ .............................. A01N 37/18; A01N 47/10
[52] U.S. Cl. .......................... 514/491; 514/476; 514/613
[58] Field of Search ...................................... 514/491, 476, 514/613

[56] References Cited

U.S. PATENT DOCUMENTS

| 5,059,623 | 10/1991 | Krüger et al. | 514/613 |
| 5,439,926 | 8/1995 | Dutzmann et al. | 514/383 |
| 5,532,262 | 7/1996 | Brandes et al. | 514/388 |

*Primary Examiner*—Allen J. Robinson
*Attorney, Agent, or Firm*—Sprung Kramer Schaefer & Briscoe

[57] ABSTRACT

There are described new active compound combinations of a compound of the formula (I)

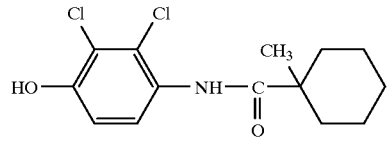

(I)

with known fungicidal active compounds, and their use for combating phytopathogenic fungi.

3 Claims, No Drawings

FUNGICIDAL ACTIVE COMPOUND COMBINATIONS

This application is a continuation of application Ser. No. 08/771,359, filed Dec. 16, 1996, now abandoned, which is a continuation Ser. No. 08/541,777, filed Oct. 10, 1995 now abandoned.

The present application relates to new active compound combinations which are composed, on the one hand, of a compound of the formula I

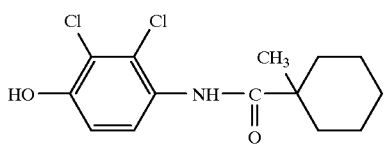

and, on the other hand, of other known fungicidal active compounds and which are highly suitable for combating phytopathogenic fungi.

It has already been disclosed that the compound of the formula (I) has fungicidal properties (cf. EP-A 339418). The activity of the substance is good; however, it leaves something to be desired in some cases when used at low application rates.

It has furthermore already been disclosed that a large number of azol derivatives, aromatic carboxylic acid derivatives, morpholin compounds and other heterocycles can be employed for combating fungi (cf. K. H. Büchel "Pflanzenschutz und Schädlingsbekämpfung" [Plant Protection and Pest Control], pages 87, 136, 140, 141 and 146 to 153, Georg Thieme Verlag, Stuttgart 1977). However, the action of the substances in question is not always satisfactory when used at low application rates.

It has now been found that the new active compound combinations of a compound of the formula I

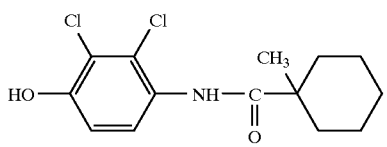

and
(A) bupyrimate (Nimrod) and/or
(B) carbozoline (Serinal) and/or
(C) quinomethionate and/or
(D) cyprodinyl and/or
(E) dinocap and/or
(F) epoxiconazole and/or
(G) fenpropidin and/or
(H) fenpiclonil and/or
(I) fluquinconazole and/or
(K) guazatine and/or
(L) 8-(1,1-dimethylethyl)-N-ethyl-N-propyl-1,4-dioxaspiro[4,5]decane-2-methaneamine and/or
(M) (E)-α-(methoxyimino)-N-methyl-2-phenoxy-benzacetamide and/or
(N) (E)-α-(methoxyimono)-N-methyl-2-(2,5-dimethyl-phenoxy-methyl)-benzacetamide and/or
(O) 1-methylethyl [2-methyl-1-[[[1-(4-methylphenyl)ethyl]amino]carbonyl]propyl]-carbamate and/or
(P) N-[5-(2-methoxy-pyridinyl)]-cyclopropane-carboxamide and/or
(Q) bromuconazole and/or
(R) organic Cu preparations, and/or Cu oxyquinolate and/or inorganic Cu preparations, with the exception of Cu oxychloride, and/or
(S) cyproconazole and/or
(T) diniconazole and/or
(U) dodine and/or
(V) ethirimol and/or
(W) fenarimol and/or
(X) fenbuconazole and/or
(Y) fenpiclonil and/or
(Z) fentin acetate and fentin hydroxide and/or
(α) imazalil and/or
(β) imibenconazole and/or
(χ) kasugamycin and/or
(δ) maneb and/or
(ε) metconazole and/or
(ω) nuarimol and/or
(π) oxycarboxin and/or
(I) polyoxin and/or
(II) propamocarb and/or
(III) propiconazole and/or
(IV) pyrazophos and/or
(V) pyrifenox and/or
(VI) tetraconazole and/or
(VII) thiabendazole and/or
(VIII) triazoxide and/or
(IX) triflumizole and/or
(X) triforine and/or
(XI) triticonazole and/or
(XII) zineb and/or
(XIII) ziram and/or
(XIV) cis-1-(4-chlorophenyl)-2-(1H-1,2,4-triazol-1-yl)-cycloheptanol and/or
(XV) diethirimol and/or
(XVI) edifenphos and/or
(XVII) fluoromide and/or
(XVIII) perfurazoate and/or
(XIX) pencycuron
have very good fungicidal properties which complement each other as synergists.

The active compound of the formula (I) has been disclosed (EP-A-339 418). The components also present in the combinations according to the invention are equally known.

Besides the active compound of the formula (I), the active compound combinations according to the invention comprise at least one active compound from amongst compounds (A) to (XIX). Preferred components in the mixture are compounds (A) to (P). In addition, the mixture may also comprise other fungicidally active components.

The synergistic effect is particularly pronounced when the active compounds are present in the active compound combinations according to the invention in certain ratios by weight. However, the ratios by weight of the active compounds in the active compound combinations can be varied within a relatively wide range. In general, 0.01 to 50, preferably 0.25 to 20, parts by weight of compounds (A) to (XIX) are used per part by weight of active compound of the formula (I).

In particular, the number of parts by weight of the components in the mixture which are used per part by weight of the compound of the formula (I) are as indicated below:

(A) 0.1 to 50, preferably 0.25 to 20,
(B) 0.1 to 50, preferably 0.25 to 20,
(C) 0.1 to 50, preferably 0.1 to 20,
(D) 0.1 to 50, preferably 0.25 to 10,
(E) 0.1 to 50, preferably 0.25 to 20,
(F) 0.01 to 10, preferably 0.025 to 5,
(G) 0.1 to 50, preferably 0.25 to 20,
(H) 0.01 to 10, preferably 0.025 to 5,
(I) 0.01 to 20, preferably 0.025 to 20,
(K) 0.01 to 20, preferably 0.025 to 20,
(L) 0.1 to 50, preferably 1 to 50,
(M) 0.01 to 10, preferably 0.025 to 10,
(N) 0.01 to 10, preferably 0.025 to 10,
(O) 0.1 to 50, preferably 0.5 to 50,
(P) 0.1 to 50, preferably 0.1 to 20,
(Q) 0.01 to 10, preferably 0.025 to 5,
(R) 1 to 50, preferably 1 to 20,
(S) 0.01 to 10, preferably 0.025 to 5,
(T) 0.01 to 10, preferably 0.025 to 5,
(U) 0.1 to 50, preferably 0.25 to 20,
(V) 0.1 to 50, preferably 0.25 to 20,
(W) 0.1 to 50, preferably 0.25 to 20,
(X) 0.01 to 10, preferably 0.025 to 5,
(Y) 0.01 to 10, preferably 0.025 to 5,
(Z) 0.1 to 50, preferably 0.25 to 20,
($\alpha$) 0.01 to 10, preferably 0.025 to 5,
($\beta$) 0.01 to 10, preferably 0.025 to 5,
($\chi$) 0.1 to 50, preferably 0.25 to 20,
($\delta$) 0.1 to 50, preferably 0.25 to 20,
($\epsilon$) 0.01 to 10, preferably 0.025 to 5,
($\omega$) 0.1 to 50, preferably 0.25 to 20,
($\pi$) 0.1 to 50, preferably 0.25 to 20,
(I) 0.1 to 50, preferably 0.25 to 20,
(II) 0.1 to 50, preferably 0.25 to 20,
(III) 0.01 to 10, preferably 0.025 to 5,
(IV) 0.1 to 50, preferably 0.25 to 20,
(V) 0.1 to 50, preferably 0.25 to 20,
(VI) 0.01 to 10, preferably 0.025 to 5,
(VII) 0.01 to 10, preferably 0.025 to 5,
(VIII) 0.1 to 50, preferably 0.25 to 20,
(IX) 0.01 to 10, preferably 0.025 to 5,
(X) 0.1 to 50, preferably 0.25 to 20,
(XI) 0.01 to 10, preferably 0.025 to 5,
(XII) 0.1 to 50, preferably 0.25 to 20,
(XIII) 0.1 to 50, preferably 0.25 to 20,
(XIX) 0.1 to 50, preferably 0.25 to 20,
(XV) 0.1 to 50, preferably 0.25 to 20,
(XVI) 0.1 to 50, preferably 0.25 to 20,
(XVII) 0.1 to 50, preferably 0.25 to 20,
(XVIII) 0.1 to 50, preferably 0.25 to 20, and
(XIX) 0.1 to 50, preferably 0.25 to 20.

The active compound combinations according to the invention have very good fungicidal properties and can be employed mainly for combating phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for combating cereal diseases, such as Erysiphe, Cochliobolus, Pyrenophora and Leptosphaeria, and against fungal attack in vegetables, grape vines and fruit, for example against Venturia in applies, Botrytis in beans and Phytophthora in tomatoes.

The good tolerance, by plants, of the active compound combinations at the concentrations required for combating plant diseases permits treatment of above-ground parts of plants, of vegetative propagation materials and seed, and of the soil.

The active compound combinations according to the invention can be converted into the customary formulations, such as solutions, emulsions, suspensions, powders, foams, pastes, granules, aerosols, very find capsules in polymeric substances and in coating compositions for seed, as well as ULV formulations.

These formulations are produced in a known manner, for example by mixing the active compounds, or active compound combinations, with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compound combinations according to the invention can be present in the formulations as a mixture with other known active compounds, such as fungicides, insecticides, acaricides and herbicides, as well as in mixtures with fertilizers or plant growth regulators.

The active compound combinations can be used as such or in the form of their formulations or the use forms prepared therefrom, such as ready-to-use solutions, emulsifiable concentrates, emulsions, suspensions, wettable powders, soluble powders and granules.

They are used in the customary manner, for example by watering, spraying, atomizing, scattering as a powder for dry seed treatment, a solution for seed treatment, a water-soluble powder for seed treatment or a water-dispersible powder for slurry treatment, or by incrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The good fungicidal, synergistically mutually complementing action of the active compound combinations according to the invention can be demonstrated by the examples which follow. While the individual active compounds show shortcomings with regard to the fungicidal activity, the activity of the combinations exceeds a simple additive effect.

A synergistic effect in fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, pages 20–22, 1967).

If

X is the degree of effectiveness expressed in % of the untreated control when applying active compound A at a concentration of m ppm, Y is the degree of effectiveness expressed in % of the untreated control when applying active compound B at a concentration of n ppm, E is the expected degree of effectiveness expressed in % of the untreated control when applying active substances A and B at a concentration of m and n ppm, then $E = X + Y - \frac{X \cdot Y}{100}$.

If the actual fungicidal activity exceeds the calculated value, then the activity of the combination is superadditive, i.e. a synergistic effect exists. In this case, the degree of effectiveness which was actually observed must be greater than the value for the expected degree of effectiveness (E) calculated from the abovementioned formula:

EXAMPLES

Botrytis test (beans)/protective

To produce a suitable preparation of active compound, either commercially available formulations of active compound (individual active compound or active compound combinations) or one part by weight of active compound is mixed with 4.7 parts by weight of solvent (acetone) and 0.3 parts by weight of emulsifier (alkyl-aryl polyglycol ether), and the mixture is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

To demonstrate synergism between the active compounds used in this experiment, the results were evaluated by the method described by Colby (see above).

Active compounds, active compound concentrations and test results can be seen from the tables which follow.

TABLE 1

Botrytis test (beans)/protective

| Active compound | Active compound concentration in ppm | Degree of effectiveness in % of the untreated control |
|---|---|---|
| (I) | 5 | 29 |
| Quinomethionate | 50 | 0 |
| Mixture according to the invention: | | |
| (I) + Quinomethionate | 5 + 50 | 63 |
| Expected value calculated by Colby's formula (see above) | | 29 |

TABLE 1a

Botrytis test (beans)/protective

| Active compound | Active compound concentration in ppm | Degree of effectiveness in % of the untreated control |
|---|---|---|
| (I) | 5 | 29 |
| Fenpropidin | 50 | 0 |
| Mixture according to the invention: | | |
| (I) | 5 | |

TABLE 1a-continued

Botrytis test (beans)/protective

| Active compound | Active compound concentration in ppm | Degree of effectiveness in % of the untreated control |
|---|---|---|
| + Fenpropidin | + 50 | 90 |
| Expected value calculated by Colby's formula (see 29 above) | | 29 |

TABLE 1b

Botrytis test (beans)/protective

| Active compound | Active compound concentration in ppm | Degree of effectiveness in % of the untreated control |
|---|---|---|
| (I) | 5 | 29 |
| Fludioxonil | 1 | 5 |
| Mixture according to the invention: | | |
| (I) + Fludioxonil | 5 + 1 | 85 |
| Expected value calculated by Colby's formula (see above) | | 33 |

TABLE 1c

Botrytis test (beans)/protective

| Active compound | Active compound concentration in ppm | Degree of effectiveness in % of the untreated control |
|---|---|---|
| (I) | 5 | 29 |
| Fluquinconazol | 25 | 29 |
| Mixture according to the invention: | | |
| (I) + Fluquinconazol | 5 + 25 | 81 |
| Expected value calculated by Colby's formula (see above) | | 50 |

TABLE 1d

Botrytis test (beans)/protective

| Active compound | Active compound concentration in ppm | Degree of effectiveness in % of the untreated control |
|---|---|---|
| (I) | 5 | 29 |
| (N) | 12.5 | 64 |
| Mixture according to the invention: | | |
| (I) + (N) | 5 + 12.5 | 85 |
| Expected value calculated by Colby's formula (see above) | | 74 |

TABLE 1e

Botrytis test (beans)/protective

| Active compound | Active compound concentration in ppm | Degree of effectiveness in % of the untreated control |
|---|---|---|
| (I) | 5 | 29 |
| (M) | 25 | 28 |
| Mixture according to the invention: | | |
| (I) + (M) | 5 + 25 | 55 |
| Expected value calculated by Colby's formula (see above) | | 49 |

TABLE 1f

Botrytis test (beans)/protective

| Active compound | Active compound concentration in ppm | Degree of effectiveness in % of the untreated control |
|---|---|---|
| (I) | 5 | 29 |
| (L) | 200 | 0 |
| Mixture according to the invention: | | |
| (I) + (L) | 5 + 200 | 78 |
| Expected value calculated by Colby's formula (see above) | | 29 |

TABLE 1g

Botrytis test (beans)/protective

| Active compound | Active compound concentration in ppm | Degree of effectiveness in % of the untreated control |
|---|---|---|
| (I) | 5 | 29 |
| (O) | 200 | 19 |
| Mixture according to the invention: | | |
| (I) + (O) | 5 + 200 | 81 |
| Expected value calculated by Colby's formula (see above) | | 42 |

TABLE 1h

Botrytis test (beans)/protective

| Active compound | Active compound concentration in ppm | Degree of effectiveness in % of the untreated control |
|---|---|---|
| (I) | 5 | 29 |
| Sodium hydroxymethyl sulphinate | 200 | 32 |
| Mixture according to the invention: | | |
| (I) + Sodium hydroxymethyl sulphinate | 5 + 200 | 86 |
| Expected value calculated by Colby's formula (see above) | | 52 |

TABLE 1i

Botrytis test (beans)/protective

| Active compound | Active compound concentration in ppm | Degree of effectiveness in % of the untreated control |
|---|---|---|
| (I) | 5 | 29 |
| Ciprodinyl | 5 | 5 |
| Mixture according to the invention: | | |
| (I) + Ciprodinyl | 5 + 5 | 46 |
| Expected value calculated by Colby's formula (see above) | | 33 |

TABLE 2

Agar plate test with Penicillium custosum

| Active compound | Active compound concentration in ppm | Degree of effectiveness in % of the untreated control |
|---|---|---|
| (I) | 100 | 24 |
| Guazatine | 100 | 9 |
| Mixture according to the invention: | | |
| (I) + Guazatine | 100 + 100 | 56 |
| Expected value calculated by Colby's formula (see above) | | 31 |

Example 2

Agar plate test with *Penicillium custosum*

Nutrient medium used:

39 parts by weight of potato dextrose agar 20 parts by weight of agar are dissolved in 1,000 ml of distilled water and the solution is kept in an autoclave at 121° C. for 20 minutes.

Solvent: 50 parts by weight of acetone 950 parts by weight of water

Ratio of the amount of solvent to nutrient medium: 1:100

To produce a suitable preparation of active compound, 1 part by weight of active compound is mixed with the stated amount of solvent.

The concentrate is thoroughly mixed, in the stated ratio, with the liquid nutrient medium, and the mixture is poured into Petri dishes.

When the nutrient medium has cooled and solidified, the plates are inoculated with the following microorganisms and are incubated at about 21° C.: *Penicillium custosum*.

Evaluation is carried out after 6 days, the inhibition of growth being used as a measure of the action of the products.

In this test, the compounds employed according to the invention perform clearly better than the prior art.

Example 3

Erysiphe test (barley)/protective

To produce a suitable preparation of active compound, commercially available formulations of active compound are diluted with water to the desired concentration.

To test for protective activity, young plants are sprayed with the preparation of active compound at the application rate shown.

After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of mildew pustules.

Evaluation is carried out 7 days after the inoculation.

TABLE 3

Erysiphe test (barley)/protective

| Active compound | Application rate of active compound in g/ha | Degree of effectiveness in % of the untreated control |
|---|---|---|
| Prior art: | | |
| (I) | 125 | 18 |
| Iminoctadine triacetate "Befran" | 125 | 27 |
| $H_2N-\overset{NH}{\underset{|}{C}}-NH-(CH_2)_8-NH-(CH_2)_8-NH-\overset{NH}{\underset{\|}{C}}-NH_2$ x (Me—COOH)$_3$ | | |
| Mixture according to the invention: | | |
| (I) + iminoctadine triacetate | 62.5 +62.5 | 55 |

Example 4

Erysiphe test (wheat)/protective

To produce a suitable preparation of active compound, commercially available formulations of active compound are diluted with water to the desired concentration.

To test for protective activity, young plants are sprayed with the preparation of active compound at the application rate shown.

After the spray coating has dried on, the plants are dusted with spores of *Erysiphe graminis* f.sp. *tritici*.

The plants are placed in a greenhouse at a temperature of about 20° C. and a relative atmospheric humidity of about 80%, in order to promote the development of mildew pustules.

Evaluation is carried out 7 days after the inoculation.

The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

TABLE 4

Erysiphe test (wheat)/protective

| Active compound | Application rate of active compound in g/ha | Degree of effectiveness in % of the untreated control |
|---|---|---|
| Prior art: | | |
| (I) | 125 | 25 |
| Quinomethionate "Morestan" | 125 | 9 |

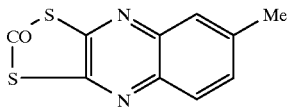

| Mixture according to the invention: | | |
|---|---|---|
| (I) + quinomethionate | 62.5 +62.5 | 41 |

Example 5

*Leptosphaeria nodorum* test (wheat)/protective

To produce a suitable preparation of active compound, commercially available formulations of active compound are diluted with water to the desired concentration.

TABLE 5

Leptosphaeria nodorum test (wheat)/protective

| Active compound | Application rate of active compound in g/ha | Degree of effectiveness in % of the untreated control |
|---|---|---|
| Prior art: | | |
| (I) | 125 | 57 |
| Epoxiconazole "Opus" | 125 | 57 |

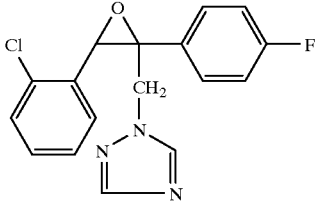

| Mixture according to the invention: | | |
|---|---|---|
| (I) + epoxiconazole | 62.5 +62.5 | 100 |

To test for protective activity, young plants are sprayed with the preparation of active compound at the application rate shown.

After the spray coating has dried on, the plants are sprayed with a spore suspension of *Leptosphaeria nodorum*.

Example 6

Erysiphe test (barley)/curative

To produce a suitable preparation of active compound, commercially available formulations of active compound are diluted with water to the desired concentration.

To test for curative activity, young plants are dusted with spores of *Erysiphe graminis* f.sp. *hordei*. 48 hours after the inoculation, the plants are sprayed with the preparation of active compound at the application rate shown.

The plants are placed in a greenhouse at a temperature of about 20° C. and a relative atmospheric humidity of about 80%, in order to promote the development of mildew pustules.

Evaluation is carried out 7 days after the inoculation.

To demonstrate synergism between the active compounds used in this experiment, the results were evaluated by the method described by R. S. Colby (Calculating Synergistic and Antagonistic Responses of Herbicides Combinations: Weeds 15, 20–22, 1967). The expected degree of effectiveness in % of the untreated control was calculated using the equation $$E = x + y - \frac{x \cdot y}{100}$$

in which x and y denote, respectively, the degree of effectiveness—expressed in % of the untreated control—obtained by the two preparations when used separately. If the actually observed degree of effectiveness of the active compound combination exceeds the value calculated for the expected degree of effectiveness (E) using the abovementioned formula, then there is a superadditive, i.e. synergistic, effect.

Example 7

*Fusarium nivale* test (wheat)/seed treatment

The active compounds are used as a powder for dry seed treatment. They are prepared by extending the active compound in question with rock meal to give a finely pulverulent mixture which guarantees uniform distribution on the seed surface.

To carry out the seed treatment, the infected seed and the seed-dressing product are shaken for 3 minutes in a sealed glass flask.

2×100 wheat kernels are sown in standard soil at a depth of 1 cm and grown in the greenhouse at a temperature of approximately 10° C. and a relative atmospheric humidity of approximately 95% in seed boxes which are exposed to the light for 15 hours per day.

Approximately 3 weeks after sowing, the plants are evaluated for snow blight symptoms.

TABLE 6

Erysiphe test (barley)/curative

| Active compound | Application rate of active compound in g/ha | Degree of effectiveness in % of the untreated control |
|---|---|---|
| Prior art: | | |
| (I) | 20 | 25 |
| 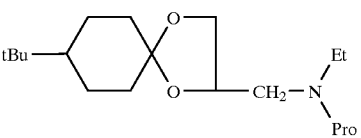 | 10 | 66 |
| Mixture according to the invention: | actually observed degree of effectiveness after using the mixture, in % of the untreated control | expected degree of effectiveness (E) after using the mixture, in % of the untreated control |
| (I) + KWG 4168 | 100<br>20<br>+10 | 75 |

TABLE 7

Fusarium nivale test (wheat)/seed treatment

| Active compound | Application rate of active compound in mg/kg of seed | Degree of effectiveness in % of the untreated control |
|---|---|---|
| Prior art: | | |
| (I) | 100 | 22 |
|  | 25 | 0 |
| Guazatine | 100 | 55 |

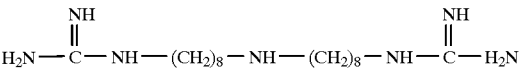

| Fenpiclonil "CGA 142705" | 25 | 6 |

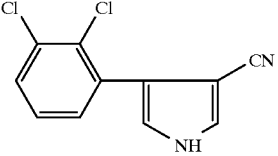

| Mixture according to the invention: | | |
| (I) + guazatine | 50 +50 | 65 |
| (I) + fenpiclonil | 12.5 +12.5 | 31 |

Example 8

Drechslera graminea test (barley)/seed treatment (syn. Helminthosporium gramineum)

The active compounds are used as a powder for dry seed treatment. They are prepared by extending the active compound in question with rock meal to give a finely pulverulent mixture which guarantees uniform distribution on the seed surface.

To carry out the seed treatment, the infected seed and the seed-dressing product are shaken for 3 minutes in a sealed glass flask.

The seed, embedded in screened, moist standard soil in sealed Petri dishes, is exposed to a temperature of 4° C. for 10 days in a refrigerator. This triggers germination of the barley and, if appropriate, of the fungal spores. 2×50 pregerminated barley kernels are subsequently sown in standard soil at a depth of 3 cm and grown in a greenhouse at a temperature of approximately 18° in seed boxes which are exposed to the light for 15 hours per day.

Approximately 3 weeks after sowing, the plants are evaluated for symptoms of barley leaf stripe.

TABLE 8

Drechslera graminea test (barley)/seed treatment (syn. Helminthosporium gramineum)

| Active compound | Application rate of active compound in mg/kg of seed | Degree of effectiveness in % of the untreated control |
|---|---|---|
| Prior art: | | |
| (I) | 100 | 43 |
|  | 50 | 41 |
| Ethirimol | 100 | 8 |

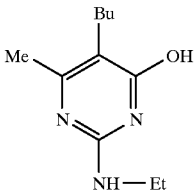

TABLE 8-continued

*Drechslera graminea* test (barley)/seed treatment
(syn. *Helminthosporium gramineum*)

| Active compound | Application rate of active compound in mg/kg of seed | Degree of effectiveness in % of the untreated control |
|---|---|---|
| Fenpiclonil "CGA 142705" | 50 | 41 |

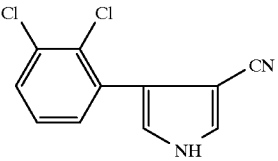

Mixture according to the invention:

| | | |
|---|---|---|
| (I) + ethirimol | 50 +50 | 54 |
| (I) + fenpiclonil | 25 +25 | 69 |

We claim:

1. A fungicidal composition comprising a syneigistic fungicidally effective amount of a combination of a first compound and a second compound, wherein said first compound is a compound of the formula (I):

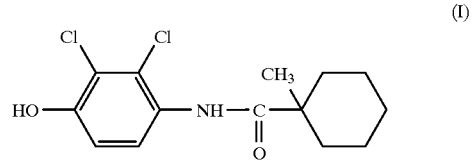

and said second compound is selected from the group consisting of maneb (δ), zineb (XII) and ziram (XIII), and wherein said second compound is present in said fungicidal composition in an amount ranging from 0.1 to 50 parts by weight per part by weight of said first compound in said fungicidal composition.

2. A fungicidal composition according to claim 1, which comprises a compound of the formula (I) and ziram (XIII).

3. A method of combating fungi comprising applying to the fungi or their environment a synergistic fungicidally effective amount of a fungicidal composition according to claim 1.

* * * * *